(12) United States Patent
Bacher et al.

(10) Patent No.: US 10,292,783 B2
(45) Date of Patent: May 21, 2019

(54) OPHTHALMIC ILLUMINATION SYSTEM WITH LIGHT INTENSITY CONTROL ON INDIVIDUAL ILLUMINATION FIBERS

(71) Applicant: NOVARTIS AG, Basel (CH)

(72) Inventors: Gerald D. Bacher, Carlsbad, CA (US);
Steven T. Charles, Memphis, TN (US);
Eyad Ammari, Irvine, CA (US); Paul Hallen, Colleyville, TX (US); Michael Papac, North Tustin, CA (US); Ronald T. Smith, Irvine, CA (US)

(73) Assignee: Novartis AG, Basel (CH)

( * ) Notice: Subject to any disclaimer, the term of this patent is extended or adjusted under 35 U.S.C. 154(b) by 434 days.

(21) Appl. No.: 14/723,654

(22) Filed: May 28, 2015

(65) Prior Publication Data

US 2016/0346058 A1   Dec. 1, 2016

(51) Int. Cl.
*A61B 90/30* (2016.01)
*A61B 3/12* (2006.01)
*A61B 90/98* (2016.01)
*A61F 9/007* (2006.01)
*A61B 3/00* (2006.01)
*A61B 17/00* (2006.01)

(52) U.S. Cl.
CPC ............ *A61B 90/30* (2016.02); *A61B 3/0008* (2013.01); *A61B 3/12* (2013.01); *A61B 90/98* (2016.02); *A61F 9/00736* (2013.01); *A61B 2017/00225* (2013.01); *A61B 2090/306* (2016.02)

(58) Field of Classification Search
CPC .... A61B 2018/2211; A61B 2018/2216; A61B 2018/2222; A61B 2018/2227; A61B 2018/2272; A61B 2018/204; A61B 1/00117; A61B 1/00126
USPC ............. 351/200, 214, 241; 606/11, 13
See application file for complete search history.

(56) References Cited

U.S. PATENT DOCUMENTS

| | | | | | |
|---|---|---|---|---|---|
| 5,463,710 | A | * | 10/1995 | Filgas | G02B 6/4225 385/44 |
| 7,414,793 | B2 | * | 8/2008 | Cianciotto | G02B 6/29362 359/618 |
| 7,568,619 | B2 | * | 8/2009 | Todd | G06Q 10/087 235/375 |
| 7,934,648 | B2 | | 5/2011 | Charles et al. | |

(Continued)

FOREIGN PATENT DOCUMENTS

GB   1280339 A   *   7/1972   ........... G02B 6/0005

*Primary Examiner* — Stephone B Allen
*Assistant Examiner* — Travis S Fissel

(57) ABSTRACT

An ophthalmic illumination system includes a light source generating a source light beam and a beam splitter splitting the source light beam into first and second light beams. A first attenuator is located in a path of the first light beam and a second attenuator is located in the path of the second light beam, the first and second attenuators operable to change the intensities of the first and second light beams, respectively. A first optical fiber port is configured for connection to a first optical fiber for delivering the first light beam to a patient's eye and a second optical fiber port is configured for connection to a second optical fiber for delivering the second light beam to the patient's eye. A control unit is communicatively coupled to the first and second attenuators and is operable to adjust the attenuators to control the intensities of the light beams delivered to the patient's eye.

20 Claims, 4 Drawing Sheets

(56) References Cited

U.S. PATENT DOCUMENTS

| | | | | |
|---|---|---|---|---|
| 8,210,728 B2* | 7/2012 | Tsutsui | ............... | G01N 21/6428 |
| | | | | 315/151 |
| 2008/0137362 A1* | 6/2008 | Gjettermann | ........ | G02B 6/0008 |
| | | | | 362/572 |
| 2010/0157620 A1* | 6/2010 | Bhadri | .................... | A61B 3/13 |
| | | | | 362/554 |
| 2011/0292344 A1* | 12/2011 | Papac | .................. | A61B 3/0008 |
| | | | | 351/221 |
| 2014/0066723 A1* | 3/2014 | Horvath | .................. | A61B 1/07 |
| | | | | 600/249 |

* cited by examiner

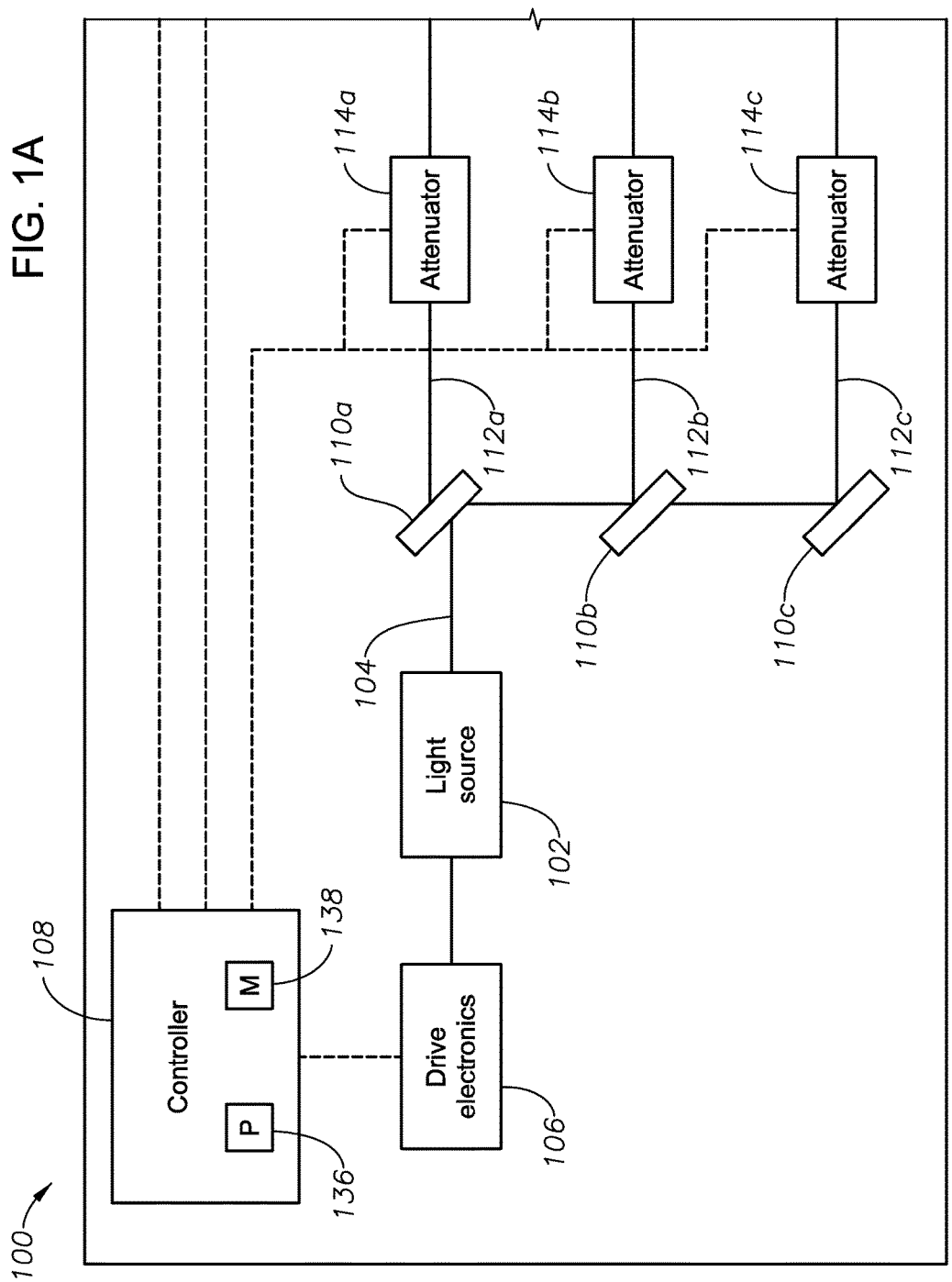

OPHTHALMIC ILLUMINATION SYSTEM WITH LIGHT INTENSITY CONTROL ON INDIVIDUAL ILLUMINATION FIBERS

FIELD

The present disclosure relates generally to the field of ophthalmic illumination systems and, more particularly, to an ophthalmic illumination system with light intensity control on individual illumination fibers.

BACKGROUND

Anatomically, an eye may be divided into two distinct parts—an anterior segment and a posterior segment. The anterior segment includes a lens and extends from an outermost layer of the cornea (the corneal endothelium) to the posterior surface of the lens capsule. The posterior segment includes the portion of the eye behind the lens capsule. The posterior segment extends from an anterior hyaloid face (part of the vitreous body) to the retina, with which a posterior hyaloid face is in direct contact. The posterior segment is much larger than the anterior segment and includes retinal pigment epithelium and choroid, both under the retina.

The posterior segment includes the vitreous body, a clear, gel-like substance composed of approximately 1% collagen and sodium hyaluronate and 99% water that makes up approximately two-thirds of the eye's volume. The anterior boundary of the vitreous body is the anterior hyaloid face, which touches the posterior capsule of the lens. The posterior boundary of the vitreous body is the posterior hyaloid face, which is in contact with the retina. The vitreous body is not free flowing like the aqueous humor and has normal anatomic attachment sites. One of these sites is the vitreous base, which is an approximately 3-4 mm wide band that overlies the ora serrata. The optic nerve head, macula, and vascular arcade are also sites of relative attachment. The vitreous body's major functions are to hold the retina in place, maintain the integrity and shape of the globe, absorb shock due to movement, and to give support for the lens posteriorly.

Various surgical procedures, called vitreo-retinal procedures, are commonly performed in the posterior segment of the eye to treat a number of serious conditions affecting the posterior segment. Vitreo-retinal procedures treat conditions such as diabetic retinopathy and diabetic vitreous hemorrhage, macular hole, epimacular membrane, vitreomacular traction, retinal detachment, trauma, and many other ophthalmic conditions. A surgeon may perform vitreo-retinal procedures with a microscope and special lenses designed to provide a clear image of the posterior segment. Several small incisions (approximately a millimeter in length) may be made on the sclera at the pars plana to allow the surgeon to insert microsurgical instruments into the posterior segment. For example one or more fiber optic light sources may be inserted to illuminate inside the eye, an infusion line may be inserted to maintain the eye's shape during surgery, and vitrectomy probe may be inserted to cut and remove the vitreous body.

During vitreo-retinal procedures, proper illumination of the inside of the eye is important. In certain conventional systems, a light source, such as a halogen tungsten lamp or high pressure arc lamp (metal-halides, Xe), may be used to produce light that is coupled to an optical fiber (e.g., via one or more lenses, mirrors, and/or attenuators), and the optical fiber may be inserted into the eye to provide the illumination. One disadvantage of these conventional systems is the relatively short life of halogen tungsten lamps and high pressure arc lamps, leading to the need to exchange lamps several times over the life of the system. Additionally, illumination provided by a single, dedicated illumination fiber may be insufficient, particularly as the diameter of such fibers decreases. The present disclosure is directed to an illumination system that addresses one or more of these disadvantages.

SUMMARY

In certain embodiments, an ophthalmic illumination system includes a light source generating a source light beam and a beam splitter splitting the source light beam into first and second light beams. A first attenuator is located in a path of the first light beam and a second attenuator is located in the path of the second light beam, the first and second attenuators operable to change the intensities of the first and second light beams, respectively. A first optical fiber port is configured for connection to a first optical fiber for delivering the first light beam to a patient's eye and a second optical fiber port is configured for connection to a second optical fiber for delivering the second light beam to the patient's eye. A control unit is communicatively coupled to the first and second attenuators and is operable to adjust the attenuators to control the intensities of the light beams delivered to the patient's eye. In certain embodiments, the control unit may collectively adjust both the first and second attenuators such that the combined intensity of the light beams delivered to the patient's eye does not exceed a maximum permissible exposure of the patient's eye.

In certain embodiments, the first optical fiber is integrated with a first surgical instrument connected to the first port and the second optical fiber is integrated with a second surgical instrument connected to the second port. The first surgical instrument may include a first radio frequency identification (RFID) tag operable to store and transmit data specific to the first surgical instrument (e.g., optical transmission characteristics of the first optical fiber when integrated with the first surgical instrument) and the second surgical instrument having a second RFID tag operable to store and transmit data specific to the second surgical instrument (e.g., optical transmission characteristics of the second optical fiber when integrated with the second surgical instrument). Additionally, the ophthalmic illumination system may further include a receiver operable to receive the data specific to the first surgical instrument transmitted by the first RFID tag and the data specific to the second surgical instrument transmitted by the second RFID tag. Based on this data, the controller may adjust the first and second attenuators in a manner that accounts for the optical transmission characteristic of the first and second optical fibers, respectively.

Certain embodiments of the present disclosure may provide one or more technical advantages. For example, certain embodiments of the present disclosure may provide an ophthalmic illumination system in which light produced by a single light source (e.g., a supercontinuum laser) is split among a plurality of optical fibers (e.g., nano fibers) each of which may be integrated into a particular surgical instrument (e.g., a sclerotomy cannula, a vitreous cutter, an illumination probe, forceps, scissors, a spatula, a pic, laser probe, etc.). As a result, multiple intraocular illumination sources may be provided without a need to increase the number of incisions in the eye to facilitate the use of multiple dedicated illumination devices. Multiple intraocular illumination sources may facilitate better visualization of the vitreous, the retina, the inner limiting membrane, and the epiretinal membrane as compared to a conventional single illumination source, which may lead to more complete vitreous removal and better surgical outcomes. Furthermore, the ability to independently control the intensity of light delivered by each of the plurality of optical fibers may further optimize visualization during surgery. In addition, the independent control of the intensity of light delivered by each of the plurality of optical fibers may be performed in a manner that maintains total light exposure of the patient's eye below a maximum permissible exposure level, which may increase patient safety during vitreo-retinal surgery.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIGS. 1A-1B illustrate an exemplary ophthalmic illumination system, according to certain embodiments of the present disclosure.

Figure 1B:
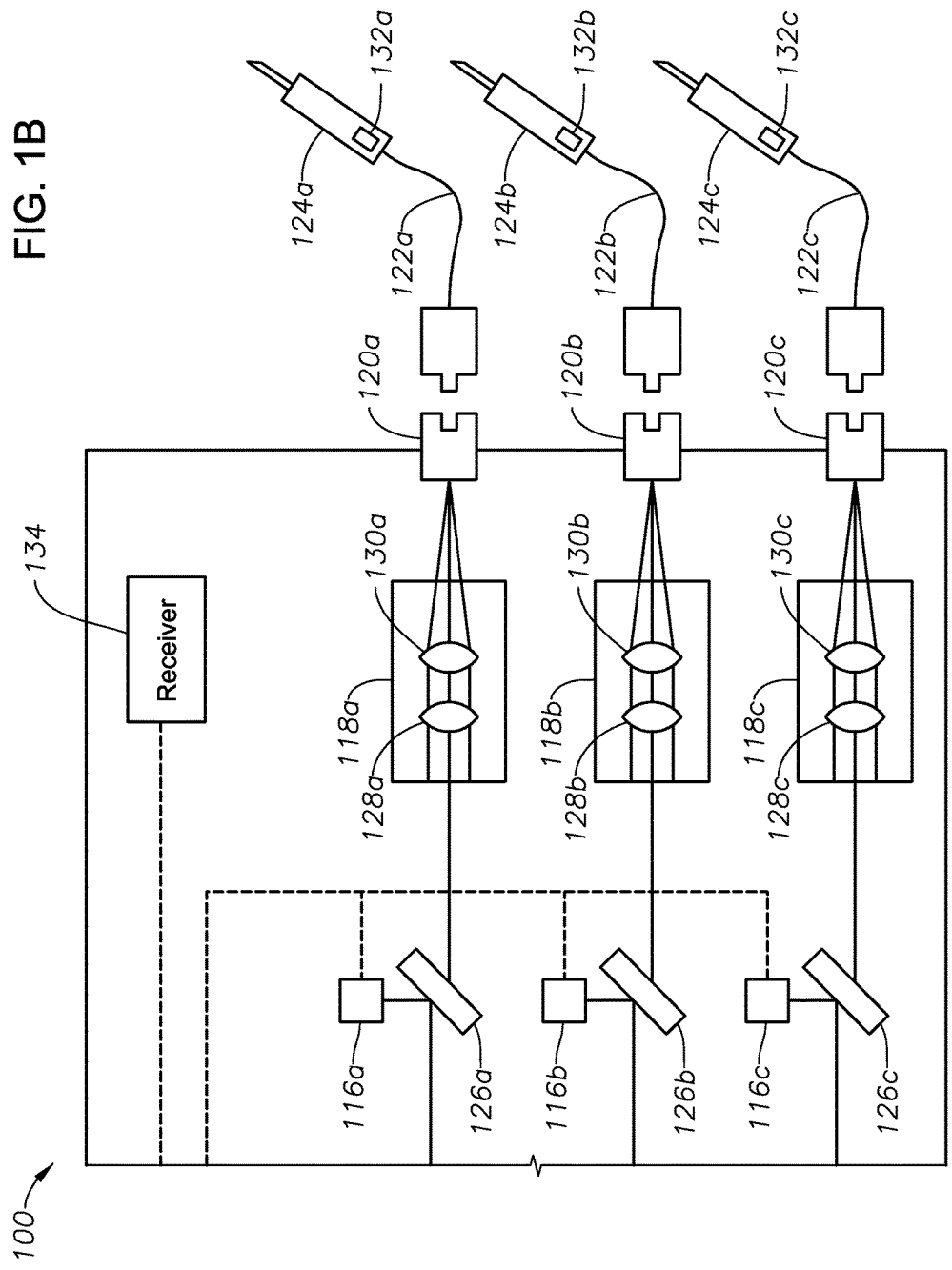

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It should nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure may provide an ophthalmic illumination system in which a source light beam emitted from a single light source is divided into a plurality of separate light beams each provided to an individual fiber port. Individual optical fibers (each of which may be integrated with a particular surgical instrument) may connect to the fiber ports and may deliver the separate light beams to a patient's eye to provide surgical illumination. Additionally, a dedicated attenuator may be provided in the path of each of the plurality of light beams such that the intensity of the light supplied to the eye via each of the optical fibers may be independently controlled.

FIGS. 1A-1B illustrate an exemplary ophthalmic illumination system 100, according to certain embodiments of the present disclosure. In certain embodiments, ophthalmic illumination system 100 may integrated into a larger surgical console facilitating ophthalmic surgery. For example, ophthalmic illumination system 100 may integrated into a surgical console including any suitable components for facilitating vitreo-retinal surgery, refractive surgery, cataract surgery, or any other suitable ophthalmic surgery.

In general, ophthalmic illumination system 100 includes a single light source 102 operable to emit a source light beam 104 (e.g., based on drive signals produced by drive electronics 106 and/or controller 108) and a plurality of beam splitters 110 operable to divide the source light beam 104 into a plurality of separate light beams 112. An attenuator 114 may be placed in the path of each of the plurality of light beams 112 to change the intensity of the light beams 112 (e.g., based on signals from a controller 108, as discussed in further detail below), and a power monitor 116 (e.g., a photodetector) may measure the intensity of each of the plurality of attenuated light beams 112 to ensure that each beam 112 has the desired intensity (facilitating closed-loop control by controller 108, as discussed further below). Optical couplers 118 may couple the attenuated light beams 112 to corresponding fiber ports 120 configured for connection to optical fibers 122, the optical fibers 122 delivering the attenuated light beams 112 to a patient's eye for surgical illumination. In certain embodiments, optical fibers 122 may be integrated with various surgical instruments 124 used for a particular surgical procedure such that multiple illumination sources may be utilized during the particular operation (which may facilitate better visualization) without the need to increase the number incisions in the eye.

Light source 102 of ophthalmic illumination system 100 may include any suitable light source operable to generate a broad spectrum source light beam 104 suitable for ophthalmic illumination. For example, light source 102 may be a supercontinuum laser source, which may produce a generally broadband white light covering a relatively wide spectral range by passing a generally narrow bandwidth pulsed pump beam through a dispersive, non-linear medium, such as a photonic crystal fiber. As the pump beam propagates through the dispersive, non-linear medium, a series of non-linear processes act upon the pump beam to cause spectral broadening of the initial pump beam, resulting in a spectral continuum extending over all or a desired portion of the visible spectrum. As another example, light source 102 may comprise a plurality of narrow spectrum laser sources that are combined to generate a broad spectrum source light beam 102. Such a light source 102 may include any suitable number of laser sources each producing light having any suitable optical properties such that the combined source light beam 102 covers all or a desired portion of the visible spectrum. Although particular examples of light source 102 have been described, the present disclosure contemplates that light source 102 may include any other suitable light source for producing a source light beam 104.

In certain embodiments, light source 102 may be communicatively coupled (e.g., via wired or wireless communication) to one or more other components for controlling the output of light source 102. For example, light source 102 may be communicatively coupled to drive electronics 106, which may drive light source 102 at a particular power and/or frequency such that source light beam 104 has the desired optical characteristics. In certain embodiments, controller 108 may control drive electronics 106 based on various informational inputs received by controller 108, including but not limited to, various user inputs and/or power signals measured by power monitors 116 (described in further detail below). Based on these inputs along with any suitable logical rules or processes that may be applied to those inputs, controller 108 may generate outputs that influence operation of drive electronics 106, thereby influencing the characteristics of source light beam 104

Ophthalmic illumination system 100 may further include one or more optical components to divide the source light beam 104 generated by light source 102 into a plurality of separate light beams 112. For example, ophthalmic illumination system 100 may include a series of beam splitters 110 operable to divided source light beam 110 into a plurality of light beams 112, each of the plurality of light beams covering substantially the same spectral range as source light beam 102 and having a portion of the overall intensity of source light beam 104. Although a particular number of beam splitters 110 are depicted as splitting source light beam into a particular number of separate light beams 112, the present disclosure contemplates any suitable component or number of components for splitting source light beam into any suitable number of separate light beams 112, according to particular needs.

Ophthalmic illumination system 100 may further include a plurality of attenuators 114, each attenuator 114 being located in the path of a corresponding one of the light beams 112. Each attenuator 114 may include any suitable device operable to change the intensity of the corresponding light beam 112. Example attenuators include, but are not limited to, variable neutral density attenuators (circular or linear/wedge), cross polarization attenuators, beam defocusing elements, and/or diaphragms.

Each attenuator 112 may be coupled to a micromotor or other device operable to change the position of one or more components of the attenuator 114. For example, when attenuators 114 comprise circular neutral density filters, the radial position of the filter may be changed via a micromotor. Because with the degree of attenuation applied by each attenuator 114 may be dependent on the position of those one or more components, the intensity of light beams 112 may be controlled in an automated manner. In certain embodiments, the position of attenuators 114 (and thus the intensities of light beams 112) may be controlled based on signals generated by controller 108 based on one or more inputs to controller 108, which may include user input, feedback from power monitors 116, and/or RFID signals transmitted by surgical instruments 124 (each of which is described in further detail below).

Ophthalmic illumination system 100 may further include a plurality of power monitors 116 each associated with a corresponding one of the attenuated light beams 112. Each power monitor 116 may include any suitable device operable to determine the intensity of the corresponding light beam 112. For example, each power monitor 116 may comprise a photodetector operable to receive a portion of the corresponding light beam 112 and generate an electronic signal indicative of the power (i.e., intensity) of the corresponding light beam 112.

To allow power monitors 116 to receive a portion of the corresponding light beams 112, a beam splitter 126 may be located in the path of each of the plurality of light beams 112. Beam splitters 126 may each reflect a portion (e.g., 5 percent) of the total intensity of the corresponding attenuated light beam 112 toward the corresponding power monitor 116, which may generate a signal indicative of the intensity of the received light. Based on that signal and the known proportion reflected by the beam splitter 126, the power monitor 116 (either alone or in conjunction with controller 108) may determine the intensity of the corresponding attenuated light beam 112. The determined intensities of each of the attenuated light beams 112 may be utilized by controller 108 to perform closed-loop control of attenuators 114 (as described in further detail below).

Ophthalmic illumination system 100 may further include a plurality of optical couplers 118 each comprising any suitable optical components for coupling a corresponding one of the plurality of attenuated light beams 112 to a fiber port 120. As just one example, each optical coupler 118 may include a collimator 128 and a condenser 130. Each collimator 128 may include optics operable to convert the received attenuated light beam 112 into a collimated light beam. The collimated light beam exiting collimator 128 may be directed to a condenser 130, which may include one or more lenses configured to focus the collimated light beam into a desired size (e.g., a size suitable for coupling to optical fiber 122) at a corresponding fiber port 120.

Each fiber port 120 of ophthalmic illumination system 100 may include any suitable receiving structure configured to accept an optical fiber 122 of desirable size (e.g., an optical fiber 122 having a 25 µm core) and maintain alignment between the collimated/condensed light beam and the optical fiber 122. For example, each optical fiber 122 may include an integrated connector that is configured to engage a fiber port 120 in a manner that maintains alignment between the optical fiber 122 and the condensed light beam exiting optical coupler 118.

In certain embodiments, each optical fiber 122 may be integrated into a corresponding surgical instruments 124. Example surgical instruments 124 include vitrectomy probes, trocar cannulas, infusion cannulas, illumination probes, or any other suitable surgical instruments. In embodiments in which ophthalmic illumination system 100 is integrated into a larger surgical console, certain other systems within that larger surgical console may facilitate non-illumination functionality of the surgical instruments 124 while ophthalmic illumination system 100 provides illumination via optical fibers 122 integrated into the surgical instruments 124.

In certain embodiments, one or more of the surgical instruments 124 may include an identifier 132 integrated into the surgical instrument 124. Each identifier 132 may include any suitable component or combination of components operable to store and transmit data specific to the surgical instrument 124 with which it is integrated. For example, each identifier 132 may be a radio frequency identification (RFID) tag including (1) an integrated circuit (IC) (e.g., an application specific integrated circuit (ASIC)) that includes a memory for storing the data specific to the surgical instrument 124, (2) a transponder for wirelessly transmitting all or a portion of the stored data. The data stored by an identifier 132 of a particular surgical instruments may include identification information associated with the particular surgical instrument 124 (e.g., the type, make, and or model of the surgical instrument), information regarding the optical fiber 122 integrated into the particular surgical instrument 124 (e.g., the size of the optical fiber and/or the optical transmission characteristics of the optical fiber 122) and/or any other suitable information regarding the operation of the particular surgical instrument.

In certain embodiments, ophthalmic illumination system 100 may include a receiver 134 configured to wirelessly communicate with identifiers 132 integrated with surgical instruments 124 connected to ophthalmic illumination system 100. For example, receiver 134 may include an antenna, a transceiver, and/or any other suitable communication components configured to facilitate communication of signals to and/or receipt of signals from identifiers 132. In embodiments in which identifiers 132 comprise RFID tags, the RFID system formed by receiver 134 and the RFID tags be passive (i.e., the RFID tags may be powered by a power pulse signal generated by receiver 134) or active (i.e., each RFID tag may have its own power source).

Certain of the signals received from identifiers 132 may include all or a portion of the above-described information concerning surgical instruments 124 stored by identifiers 132. Moreover, receiver 134 may be communicatively coupled (e.g., via wired or wireless communication) to controller 108 such that the received information can be communicated to controller 108. As described in further detail below, controller 108 may use the received information in controlling the position of attenuators 114 (and, as a result, the intensities of light beams 112).

Controller 108 of ophthalmic illumination system 100 may include any suitable combination of hardware, firmware, and software. In certain embodiments, controller 108 may include a processing module 136 and a memory module 138. Processing module 136 may include one or more microprocessors, controllers, or any other suitable computing devices or resources. Processing module 136 may work, either alone or with other components of ophthalmic illumination system 100, to provide the functionality described herein. Memory module 138 may take the form of volatile or non-volatile memory including, without limitation, magnetic media, optical media, random access memory (RAM), read-only memory (ROM), removable media, or any other suitable memory component.

As described above, controller 108 may be coupled, via wired or wireless communication, to one or more other components of ophthalmic illumination system 100. For example, controller 108 may be communicatively coupled to (1) a graphical user interface (not shown) or other suitable input device (e.g., keyboard, mouse, etc.) such that controller 108 may receive input from a user of ophthalmic illumination system 100, (2) power monitors 116 such that controller 108 may receive feedback signals indicating the intensities of the attenuated light beams 112, and (3) receiver 134 such that controller 108 may receive information communicated to receiver 134 by identifiers 132 of surgical instruments 124. Additionally, controller 108 may be communicatively coupled to attenuators 114 such that controller 108 may control the position of attenuators 114 (and this the intensities of light beams 112) based at least in part on the above-described information received by controller 108.

In certain embodiments, controller 108 may include an attenuation control application 140 for controlling the position of attenuators 114 (and thus the intensities of light beams 112) based on one or more inputs to controller 108. Attenuation control application 140 may include any suitable combination of software, hardware, and firmware. In order to determine appropriate positions for attenuators 114, attenuation control application 140 may access user input information (e.g., generated via a GUI or another suitable input device), intensity information generated by power monitors 116, and/or information associated with surgical tools 124 connected to ophthalmic illumination system 100 (received by receiver 134 from identifiers 132 integrated with surgical tools 124). Attenuation control application 140 may access such information by receiving it directly, by accessing it from memory module 138, or by receiving and/or retrieving it in any other suitable manner.

Based on the above-described accessed information, attenuation control application 140 may determine an appropriate position setting for each of the one or more attenuators 114 (or a subset comprising only those attenuators 114 controlling intensities of light beams 112 coupled to fiber ports to which a surgical instruments 124 are attached). For example, with respect to a particular attenuator 114 of a light beam 112 coupled to attenuation to an optical fiber 122 of a particular surgical instrument 124, attenuation control application 140 may access a user input indicating a surgeon-specified intensity to be emitted from the optical fiber 122 of the particular surgical instrument 124. Additionally, attenuation control application 140 may access information concerning the light transmission characteristics of the particular surgical instrument 124. Based at least in part on the light transmission characteristics of the particular surgical instrument 124, attenuation control application 140 may determine an appropriate intensity of the light beam 112 leaving the attenuator 114 (such that, accounting for optical transmission characteristics of the optical fiber 122, the surgeon-specified intensity reaches the patient's eye via the distal end of the optical fiber 122). To achieve the determined appropriate intensity of the light beam 112 leaving the attenuator 114, attenuation control application 140 may generate an attenuation control signal operable to cause the attenuator 114 to be set to an appropriate position such that the appropriate intensity is achieved. In certain embodiments, memory 138 may store information correlating attenuator position to the resulting intensity of the attenuated light beam 112, and the attenuation control signal may be based at least in part on that correlation information. Attenuation control application 140 may set the intensities of each of the light beams 112 in the above-described manner.

Having set attenuators 114 to the appropriate position to achieve the desired intensity in the manner described above, attenuation control application 140 may be further operable to access signals generated by power monitors 116, the accessed signals corresponding to the intensities of light beams 112 exiting attenuators 114. Attenuation control application 140 may use the accessed signals in order to perform closed-loop control of the attenuator settings. For example, with regard to a particular attenuator 114, attenuation control application 140 may access the power signal generated by the power monitor 116 measuring the intensity of the light beam 112 exiting the particular attenuator 114. Attenuation control application 140 may compare that measured intensity to the previously determined appropriate intensity needed to exit the particular attenuator 114 to achieve the desired intensity at the patient's eye and further adjust the particular attenuator 114 to achieve/maintain that appropriate intensity. Accordingly, attenuation control application 140 may facilitate closed loop control of attenuators 114.

In certain embodiments, memory module 138 may store maximum permissible exposure information indicating maximum intensity and/or duration of exposure permitted for a patient's eye during ophthalmic surgery. Attenuation control application 140 may additionally access such maximum permissible exposure information in order to ensure that the combined intensity of light reaching a patient's eye does not exceed the maximum permissible exposure of the patient's eye. For example, if the user input necessitates control of attenuators 114 such that, accounting for the light transmission characteristics of the surgical instruments 124 connected to ophthalmic illumination system 100, the total light reaching the patient's eye exceed the maximum permissible exposure level, attenuation control application 140 may initiate display of a warning (e.g., vi the GUI) to indicate to the surgeon that the intensity levels requested should be reduced. Additionally or alternatively, attenuation control application 140 may automatically reduce the combined intensity of light reaching the patient's eye by adjusting one or more of attenuators 114. As a result, in addition to individually controlling the intensities of the light beams 112 as described above, attenuation control application 140 may collectively control all of the intensities to maintain patient safety.

The above-described functionality of ophthalmic illumination system 100 may provide one or more technical advantages. For example, ophthalmic illumination system 100 may provide multiple intraocular illumination sources (via surgical instruments 124 having integrated optical fibers 122) without a need for multiple light sources 102 (reducing cost) and without the need to increase the number of incisions in the eye to facilitate the use of multiple dedicated illumination probes. Multiple intraocular illumination sources may facilitate better visualization of the vitreous, the retina, the inner limiting membrane, and the epiretinal membrane as compared to a conventional single illumination source, which may lead to more complete vitreous removal and better surgical outcomes. Furthermore, controller 108 of ophthalmic illumination system 100 may provide the ability to independently control the intensity of each of the light beams 112 coupled to each of the plurality of optical fibers 122, which may further optimize visualization during surgery. In addition, the independent control of the intensity of each of the plurality light beams 112 may be performed in a manner that maintains total exposure below a maximum permissible exposure level, which may increase patient safety during vitreo-retinal surgery.

Figure 2A:
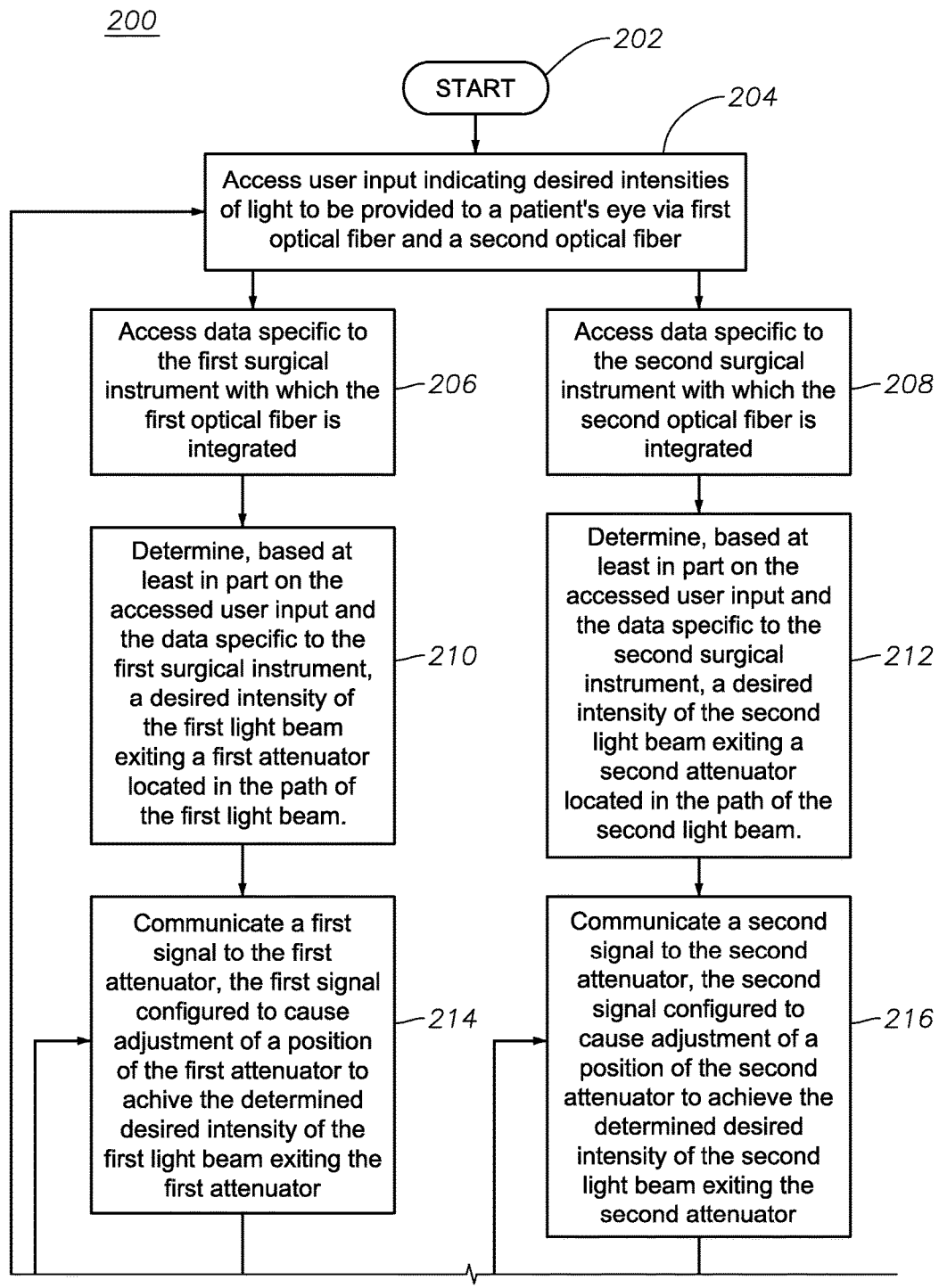
FIGS. 2A-2B illustrates an exemplary method for attenuation of multiple illumination light beams, according to certain embodiments of the present disclosure.
Figure 2B:
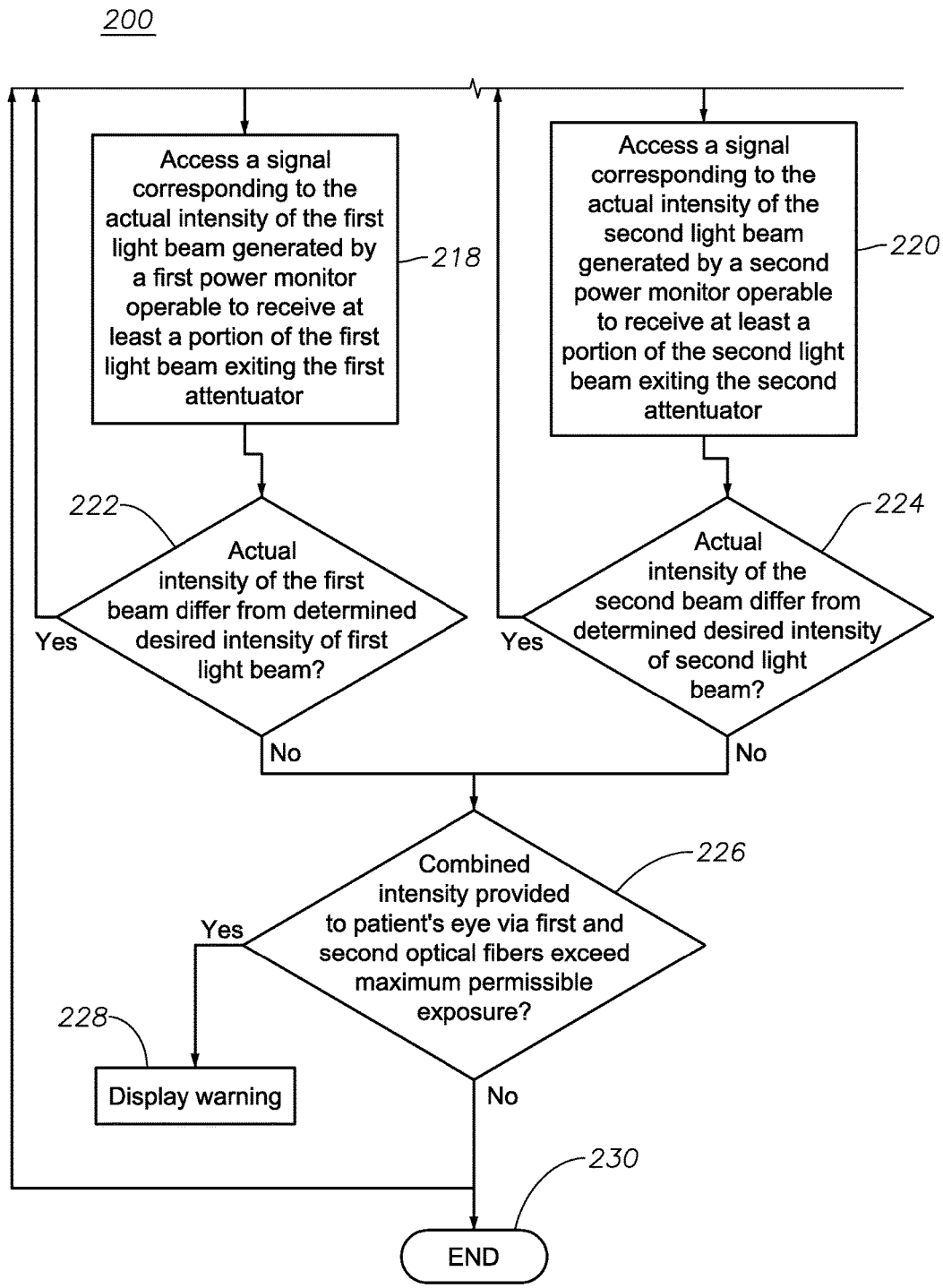

FIGS. 2A-2B illustrate an exemplary method 200 for attenuation of multiple illumination light beams 112, according to certain embodiments of the present disclosure. Although method 200 is depicted and described with regard to a system in which a source light beam 104 is divided into only two light beams 112 for simplicity, the present disclosure contemplates that the method 200 may apply to a system in which a source light beam 104 is divided into any suitable number of light beams 112, according to particular needs. Additionally, although the steps of method 200 are depicted and described in a particular order, the present disclosure contemplates that those steps may be performed in any suitable order, according to particular needs.

The method begins at step 202. At step 204, controller 108 accesses user input indicating a surgeon's desired illumination output from each of the first optical fiber 122 (e.g., optical fiber 122a) and the second optical fiber 122 (e.g., optical fiber 122b). As described above, such input may be entered by a surgeon via a GUI or any other suitable input device. At step 206, controller 108 accesses data specific to a first surgical instrument 124 with which the first optical fiber 122 is integrated (e.g., surgical instrument 124a) and, at step 208, controller 108 accesses data specific to a second surgical instrument 124 with which the second optical fiber 122 is integrated (e.g., surgical instrument 124b). As described above, the data specific to the surgical instruments 124 may be stored by identifiers 132 (e.g., RFID tags) integrated into surgical instruments 124 and communicated by those identifiers 132 to a receiver 134 of ophthalmic illumination system 100. The data may include, for example, optical transmission characteristics of the optical fibers 122 to enable controller 108 to accurately determine the intensity of light delivered to a patient's eye via those optical fibers 122.

At step 210, controller 108 determines, based at least in part of the accessed user input and the accessed data specific to the first surgical instrument 124, a desired intensity of light exiting a first attenuator 114 in the path of the first light beam 112 (e.g., attenuator 114a). Similarly, at step 212, controller 108 determines, based at least in part of the accessed user input and the accessed data specific to the second surgical instrument 124, a desired intensity of light exiting the a second attenuator 114 in the path of the second light beam 112 (e.g., attenuator 114b). In certain embodiments, the determined intensity exiting an attenuator 114 may be an intensity that accounts for the light loss characteristics of the associated optical fiber 122 (from the accessed data specific to the surgical instrument 124 with which the associated optical fiber 122 is integrated) and results in the surgeon's desired intensity (from the accessed user input) being emitted from the associated optical fiber 122 via the surgical instrument 124.

At step 214, controller 108 communicates a first signal to the first attenuator 114, the first signal configured to cause adjustment of the position of the first attenuator 114 such that the determined desired intensity of the first light beam 112 as it exits the first attenuator 114 is achieved. Similarly, at step 216, controller 108 communicates a second signal to the second attenuator 114, the second signal configured to cause adjustment of the position of the second attenuator 114 such that the determined desired intensity of the second light beam 112 as it exits the second attenuator 114 is achieved. In certain embodiments, the first and second signals may be generated based at least in part of accessed information correlating the positions of the first and second attenuators 114 to the output intensities of those attenuators 114 (such information being stored, for example, in memory module 138).

At step 218, controller 108 accesses a power signal generated by a first power monitor 116 operable to receive at least a portion of the first light beam 112 (e.g., power monitor 116a) and, at step 220, controller 108 accesses a power signal generated by a second power monitor 116 operable to receive at least a portion of the second light beam 112 (e.g., power monitor 116b). The accessed power signals may correspond to the actual intensities of the first and second light beams 112 as they exit first and second attenuators 114, respectively. At step 222, controller 108 determines if the actual intensity of the first light beam 112 exiting the first attenuator 114 differs (or differs by more than a threshold amount) from the determined desired intensity. If so, the method 200 returns to step 214 such that adjustment of the position of the first attenuator may be made. Similarly, at step 224, controller 108 determines if the actual intensity of the second light beam 112 exiting the second attenuator 114 differs (or differs by more than a threshold amount) from the determined desired intensity. If so, the method 200 returns to step 216 such that adjustment of the position of the second attenuator may be made. As a result, controller 108 may perform closed loop control of attenuators 114.

At step 226, controller 108 determines if the combined intensity of light provided to the patient's eye via the first and second optical fibers 122 (which should match or closely approximate the surgeons requested output from the user input) exceeds a maximum permissible exposure of the patient's eye. If so, a warning may be displayed to the surgeon (e.g., via the GUI) at step 228. Additionally or alternatively, attenuators 114 may be automatically adjusted by controller 108 (in a manner similar to that described above) to reduce the total intensity of light reaching the patient's eye to a point below the maximum permissible exposure level.

To the extent the surgeon requests changes to the level of light output via the first and second optical fibers 122, the method 200 returns to step 204. Otherwise, the method may end at step 230. Alternatively, the present disclosure contemplates that steps 218 through 226 may be continuously performed on a periodic basis to ensure that the desired light output is maintained and that the maximum permissible exposure is not exceeded.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic illumination system, comprising
a light source operable to generate a source light beam;
a beam splitter operable to split the source light beam into a first light beam and a second light beam;
a first attenuator located in a path of the first light beam, the first attenuator operable to change an intensity of the first light beam;
a second attenuator located in a path of the second light beam, the second attenuator operable to change an intensity of the second light beam;
a first optical fiber port configured for connection to a first optical fiber, the first optical fiber delivering at least a portion of the first light beam to a patient's eye;
a second optical fiber port configured for connection to a second optical fiber, the second optical fiber delivering at least a portion of the second light beam to the patient's eye; and
a control unit communicatively coupled to the first attenuator and the second attenuator, the control unit operable to:
adjust the first attenuator in order to control the intensity of the portion of the first light beam delivered to the patient's eye via the first optical fiber; and
adjust the second attenuator to control the intensity of the portion of the second light beam delivered to the patient's eye via the second optical fiber.

2. The ophthalmic illumination system of claim 1, wherein the light source comprises a supercontinuum laser.

3. The ophthalmic illumination system of claim 1, wherein the control unit is operable to collectively adjust both the first attenuator and the second attenuator such that a combined intensity of the portion of the first light beam delivered to the patient's eye via the first optical fiber and the portion of the second light beam delivered to the patient's eye via the second optical fiber does not exceed a maximum permissible exposure of the patient's eye.

4. The ophthalmic illumination system of claim 1, wherein the first attenuator and the second attenuator each comprise one of a cross polarization attenuator, a variable neutral density wedge, a variable circular neutral density filter, a beam defocusing element, and a diaphragm.

5. The ophthalmic illumination system of claim 1, wherein:
the first optical fiber is integrated with a first surgical instrument connected to the first port, the first surgical instrument having a first identifier operable to store and transmit data specific to the first surgical instrument;
the second optical fiber is integrated with a second surgical instrument connected to the second port, the second surgical instrument having a second identifier operable to store and transmit data specific to the second surgical instrument.

6. The ophthalmic illumination system of claim 5, wherein the first and second identifier each comprise radio frequency identification (RFID) tags.

7. The ophthalmic illumination system of claim 5, further comprising a receiver operable to receive the data specific to the first surgical instrument transmitted by the first identifier and the data specific to the second surgical instrument transmitted by the second identifier.

8. The ophthalmic illumination system of claim 5, wherein:
the data specific to the first surgical instrument comprises light transmission characteristic of the first optical fiber integrated into the first surgical instrument;
the data specific to the second surgical probe comprises light transmission characteristic of the second optical fiber integrated into the second surgical instrument; and
the controller:
adjusts the first attenuator based at least in part on the light transmission characteristic of the first optical fiber integrated into the first surgical instrument; and
adjusts the second attenuator based at least in part on the light transmission characteristic of the second optical fiber integrated into the second surgical instrument.

9. The ophthalmic illumination system of claim 1, further comprising:
a first power monitor operable to receive at least a portion of the first light beam exiting the first attenuator, the first power monitor operable to generate a signal corresponding to the intensity of the first light beam; and
a second power monitor operable to receive at least a portion of the second light beam exiting the second attenuator, the second power monitor operable to generate a signal corresponding to the intensity of the second light beam.

10. The ophthalmic illumination system of claim 9, wherein the controller is further operable to:
adjust the first attenuator based at least in part on the signal corresponding to the intensity of the first light beam generated by the first power monitor; and
adjust the second attenuator based at least in part on the signal corresponding to the intensity of the second light beam generated by the second power monitor.

11. The ophthalmic illumination system of claim 1, wherein the first optical fiber and the second optical fiber each comprise a nano fiber having a core diameter of 25 µm or less.

12. The ophthalmic illumination system of claim 1, wherein:
the first optical fiber is integrated with a first surgical instrument connected to the first port;
the second optical fiber is integrated with a second surgical instrument connected to the second port;
the first surgical instrument and the second surgical instrument each comprise one of a sclerotomy cannula, a vitreous cutter, an illumination probe, forceps, scissors, a spatula, and a pic.

13. A method for attenuation of a first light beam and a second light beam, comprising:
accessing user input indicating desired intensities of light to be provided to a patient's eye via each of a first optical fiber and a second optical fiber, the first light beam being coupled to the first optical fiber and the second light beam being coupled to the second optical fiber;

accessing data specific to a first surgical instrument and data specific to a second surgical instrument, the first optical fiber being integrated with the first surgical instrument and the second optical fiber being integrated with the second surgical instrument;

determining, based at least in part on the accessed user input and the data specific to the first surgical instrument, a desired intensity of the first light beam exiting a first attenuator located in a path of the first light beam;

determining, based at least in part on the accessed user input and the data specific to the second surgical instrument, a desired intensity of the second light beam exiting a second attenuator located in a path of the second light beam;

communicating a first signal to the first attenuator, the first signal configured to cause adjustment of a position of the first attenuator to achieve the determined desired intensity of the first light beam exiting the first attenuator; and communicating a second signal to the second attenuator, the second signal configured to cause adjustment of a position of the second attenuator to achieve the determined desired intensity of the second light beam exiting the second attenuator.

14. The method of claim 13, wherein:

the first signal is generated based at least in part on accessed information correlating the position of the first attenuator and the intensity of light exiting the first attenuator; and the second signal is generated based at least in part on accessed information correlating the position of the second attenuator and the intensity of light exiting the second attenuator.

15. The method of claim 13, further comprising:

accessing a signal corresponding to an actual intensity of the first light beam generated by a first power monitor operable to receive at least a portion of the first light beam exiting the first attenuator;

accessing a signal corresponding to an actual intensity of the second light beam generated by a second power monitor operable to receive at least a portion of the second light beam exiting the second attenuator;

comparing the actual intensity of the first light beam exiting the first attenuator to the determined desired intensity of the first light beam exiting the first attenuator; and comparing the actual intensity of the second light beam exiting the first attenuator to the determined desired intensity of the second light beam exiting the second attenuator.

16. The method of claim 13, wherein:

the data specific to the first surgical instrument comprises light transmission characteristic of the first optical fiber integrated into the first surgical instrument;

the data specific to the second surgical instrument comprises light transmission characteristic of the second optical fiber integrated into the second surgical instrument.

17. The method of claim 13, wherein the first attenuator and the second attenuator each comprise one of a cross polarization attenuator, a variable neutral density wedge, a variable circular neutral density filter, a beam defocusing element, and a diaphragm.

18. The method of claim 13, wherein:

the data specific to the first surgical instrument is stored and transmitted by a first identifier integrated into the first surgical instrument; and the data specific to the second surgical instrument is stored and transmitted by a second identifier integrated into the second surgical instrument.

19. The method of claim 18, wherein the first and second identifiers each comprise radio frequency identification (RFID) tags.

20. The method of claim 13, further comprising determining whether a total of the desired intensities of light to be provided to the patient's eye via each of the first optical fiber and the second optical fiber exceeds a maximum permissible exposure of the patient's eye.

* * * * *